United States Patent [19]
La Greca

[11] Patent Number: 6,093,703
[45] Date of Patent: Jul. 25, 2000

[54] PHARMACEUTICAL COMPOSITIONS, CONTAINING S-ADENOSYL-L-METHIONINE SALT, 5-METHYL-TETRAHYDROFOLIC ACID AND 5-FORMYLTETRAHYDROFOLIC ACID

[75] Inventor: Pietro La Greca, Villa Raverio, Italy

[73] Assignee: Bioresearch S.p.A., Milan, Italy

[21] Appl. No.: 08/108,005

[22] Filed: Aug. 18, 1993

Related U.S. Application Data

[63] Continuation of application No. 07/779,804, Oct. 21, 1991, abandoned.

[30] Foreign Application Priority Data

Oct. 23, 1990 [IT] Italy ..................................... 21833A90

[51] Int. Cl.⁷ .............................................. A61K 31/7105
[52] U.S. Cl. ........................... 514/46; 514/249; 514/254; 514/269; 514/885
[58] Field of Search ............................. 514/46, 269, 254, 514/885, 249

[56] References Cited

U.S. PATENT DOCUMENTS 5,059,595  10/1991  Le Grazie ............................... 424/468

FOREIGN PATENT DOCUMENTS

| | | |
|---|---|---|
| 0352609 | 1/1990 | European Pat. Off. . |
| 0388827 | 9/1990 | European Pat. Off. . |
| 4005275A1 | 2/1990 | Germany . |
| WO-A9007928 | 7/1990 | WIPO . |
| WO-A9112809 | 9/1991 | WIPO . |

OTHER PUBLICATIONS

Budavari et al, eds, (1989) *The Merck Index*, Merck & Co., Inc., New Jersey, pp 456–457, Eleventh Edition.
115 CA:223447v Grundmann et al. 1991.
90 CA: 3493g (3493g) Balk et al 1979.
114 CA: 75184u Jacob et al 1991.

*Primary Examiner*—Shailendra Kumar
*Attorney, Agent, or Firm*—Birch, Stewart, Kolasch & Birch, LLP

[57] ABSTRACT

For the therapy of neurological complications in AIDS sufferers, the use of pharmaceutical compositions containing as an active principle at least one compound selected from the group consisting of S-adenosyl-L-methionine salt, 5-methyl-tetrahydro-folic acid, 5-formyltetrahydro-folic acid, when the active principle consists of S-adenosyl-L-methionine and of a derivative of tetrahydro folic acid, the weight ratio between the S-adenosyl-L-methionine salt and 5-methyltetrahydrofolic acid or 5-formyl-tetrahydrofolic acid is comprised between 10/1 and 4/1, in pharmaceutical form, suitable for oral or parenteral administration.

11 Claims, 2 Drawing Sheets

GROUP 1 (MTHF + SAMe)

GROUP 2 (PLACEBO)

GROUP 3 (MTHF)

GROUP 4 (SAMe)

PHARMACEUTICAL COMPOSITIONS, CONTAINING S-ADENOSYL-L-METHIONINE SALT, 5-METHYL-TETRAHYDROFOLIC ACID AND 5-FORMYLTETRAHYDROFOLIC ACID

This application is a continuation of application Ser. No. 07/779,804 filed on Oct. 21, 1991, now abandoned.

The present invention is drawn to pharmaceutical compositions active in the therapy of neurological affections in AIDS patients, containing as an active principle at least one compound selected from the group consisting of S-adenosyl-L-methionine salt, 5-methyl-tetrahydrofolic acid, 5-formyltetrahydrofolic acid.

AIDS (Acquired Immunodeficiency Syndrome) is a transmissible infective disease of high mortality, which preferentially affects immune system cells exposing individuals to the risk of contracting multiple infections and certain types of tumors.

The virus responsible for AIDS, the HIV (Human Immunodeficiency Virus), is a retrovirus with elective trophism for T lymphocytes, especially of the phenotype OKT4/Leu 3 (helper/inducer), from which it can be isolated.

A virtually constant occurring event in subjects infected by HIV is the involvement of the Central Nervous System (CNS), which is manifested by demyelination, in the form of multifocal progressive leukoencephalopathy, with a series of symptoms ranging from slight psychic disturbance to a clear neurological syndrome.

About 10% of AIDS patients show serious neurological symptoms (aphasia, ataxia, and areflexia as far as motor incoordination with paralysis and loss of sphincteric control), and in 75%, of cases a necroscopic examination shows evident signs of involvement of the nervous system. In 62% of HIV-positive subjects organic mental disturbances are described which lead to alteration of the cognitive functions and to dementia, while as many as 83% manifest disturbances of mood (depression).

It has been reported in the literature that HIV-positive subjects with accompanying neurological complications can exhibit 5-methyl-tetrahydrofolate (MTHF) and S-adenosylmethionine (SAMe) deficiency. In particular, these patients exhibit a reduced concentration of total folates, of SAMe and methionine, and an increase in neopterin levels in the cerebrospinal fluid.

On the basis of these data it has been suggested that an alteration in the metabolism of transmethylating compounds is at the base of the neurological disturbance present in such subjects. This would in fact lead to multifocal and perivenular demyelination of the central nervous system. These are lesions totally similar to those caused by vitamin B12 deficiency (E. G. Lever et al., J. of Neurology, Neurosurgery and Psychiatry, 49: 1203–1207, 1986).

Two metabolic mechanisms of indirect toxicity would be involved:
1) The microphages persistently stimulated by the τ interferon induced by viral infection synthesize large quantities of dihydropteridine. This substance by acting as an "antifolic" is able to inhibit the metabolic paths which lead to the synthesis of MTHF and consequently SAMe (MTHF being the physiological precursor of SAMe in the central nervous system) (R. Surtees et al., The Lancet, vol 335, March 1990).
2) In addition, as folate catabolism occurs by chemical oxidation, folate depletion in the cerebrospinal fluid could also result in increased oxidative activity (I. Smith et al., The Lancet, Jul. 25, 1987).

These data suggest that folate (MTHF) and SAMe deficiency can be a cause of neurological degeneration in AIDS patients.

Administration of methionine and betaine has been suggested to correct this metabolic deficiency (The Lancet, March 1990).

We have now found that administering methionine and betaine at doses of 6 g/day for 14 days was not able to significantly increase MTHF and SAMe body fluid levels.

Specifically, we found that administering methionine and betaine to 4 subjects affected by AIDS with neurological complications did not result in improvement in the neurological clinical symptoms, or in modifications of the studied parameters related to the symptomatology, or in an increase in SAMe and MTHF body fluid levels (Table I).

However, we have surprisingly found that administering MTHF, and SAMe parenterally or orally for at least 7 days is able to significantly increase the values of these compounds in the cerebrospinal fluid and hence in the central nervous system.

The clinical trial reported below has unequivocally shown that treatment with MTHF (or FTHF) and SAMe in a group of 20 HIV-positive subjects is associated with general clinical improvement, positive modification of the studied neurological parameters and significant SAMe and MTHF increase in the cerebrospinal fluid.

In the present specification, for improved clarity and simplicity, the denomination "5-methyl-tetrahydro folic acid" and "MTHF" refer to compounds having the following complete chemical names:
(±) L-5-methyl-5,6,7,8-tetrahydro folic acid, and
(−) L-5-methyl-5,6,7,8-tetrahydro folic acid and their salts,
while, with the denomination 5-formyl-tetrahydro-folic acid and the abbreviation FTHF refer to compounds having the following complete chemical names: (±)-L-5-formyl-5,6,7,8-tetrahydro-folic acid, and (−)-L-5-formyl-5,6,7,8-tetrahydro-folic acid and their salts.

TABLE I

PATIENTS TREATED WITH METHIONINE AND BETAINE

| Patient | Age | Sex | SAMe (nmol/l) before/after | MTHF (nmol/l) before/after |
|---|---|---|---|---|
| 1 | 31 | M | 48/52 | 42/25 |
| 2 | 27 | F | 41/44 | 41/39 |
| 3 | 29 | M | 38/40 | 20/18 |
| 4 | 25 | M | 56/62 | 31/37 |

The present invention therefore relates to pharmaceutical compositions active in the therapy of neurological affections in AIDS patients, characterized by containing as an active principle at least one compound selected from the group consisting of S-adenosyl-L-methionine salt, 5-methyltetrahydro-folic acid and 5-formyl-tetrahydro-folic acid, or their salts, in association with pharmaceutically acceptable excipients.

In particular, the pharmaceutical compositions according to the present invention are active in the treatment of subacute encephalitis associated with dementia and of vacuolar myelopathies associated with neurological deficiencies which occur with great frequency during infection by HIV (Human Immunodeficiency Virus).

There is currently no effective treatment available in the therapy of neurological complications arising during the course of AIDS.

5-methyltetrahydrofolic acid, 5-formyltetrahydrofolic acid and their salts are a group of substances pertaining to the vitamin B complex, structurally related to pteroylglutamic acid (folic acid). This acid is not synthesized by mammalian cells and is of particular biological importance. In this respect, it is involved in a series of chemical reactions in the transfer of monocarbon groups, and in particular for the synthesis of the purine ring, of thymidylate and in the neogenesis of methyl groups.

In the blood circulation the folate pool is mostly represented by MTHF acid, but also by FTHF. MTHF represents the main form of transport of folates in the blood. It passes from the blood to the fluid at the choroid plexus level, and then by passive diffusion into the tissue and nerve cells. At the central nervous system level the folates and in particular MTHF participate in fundamental biochemical processes by intervening in the synthesis of S-adenosyl-L-methionine (SAMe), in the metabolism of certain amino acids (glycine, serine, glutamic acid), in modulatory activity of the monoaminergic transmission systems (noradrenaline, serotonine, dopamine), in nucleic acid synthesis and in the production of ATP and GTP.

The therapeutic use of folic acid and its cofactors has been limited up to the present time to the prevention and treatment of body deficiencies of this vitamin, ie to the treatment of hypofolatemic subjects.

The object of the present invention is to enable effective therapy of neurological disturbances related to the acquired immunodeficiency syndrome, by providing pharmaceutical compositions with demonstrated clinical effectiveness in the therapy of such disturbances and which are free of side-effects.

We have now found that oral or parenteral administration of pharmaceutical compositions containing as an active principle at least one compound selected from the group consisting of S-adenosyl-L-methionine salt, 5-methyl-tetrahydro-folic acid and 5-formyl-tetrahydro-folic acid or their salts in association with pharmaceutically acceptable excipients demonstrates unexpected pharmacological activity when used for treating subjects affected by AIDS-related neurological disturbances. For the SAMe, any of its stable salts can be used, and in particular those described in the previous Italian patent applications of the present applicant Nos. 1,022,016, 1,043,885. 1,054,175, 1,137,640, 1,137,892, 1,169,772, 1,169,773, 1,169,774, 1,173,990, 1,173,991, 1,173,992.

The three active principles can be administered as a mixture or separately.

The dosage is between 20 and 200 mg/day and preferably 50 mg/day for the MTHF (or FTHF) and between 100 and 2000 mg/day and preferably 400 mg/day for the SAMe. In addition, from clinical trials it has been found that the best results are obtained with a SAMe/MTHF (or FTHF) weight ratio of between 10/1 and 4/1, and preferably about 8/1.

The neurological disturbances during the course of AIDS can be secondary to a pathogenic noxa of infective nature, or primarily involve the central nervous system by an etiopathogenetic mechanism which is still not well understood.

In this second case the patients are affected by:
1) subacute encephalitis associated with dementia (see code 294.10, Axis I, organic mental disturbances associated with physical disturbances, see Axis III, or for which the etiology is unknown, in accordance with the criteria contained in the Diagnostic and Statistical Manual of Mental Disorders, Third Edition Revised, published by the American Psychiatric Association in 1987)
2) vacuolar myelopathy with progressive paraparesis, ataxia, spasticity and incontinence
3) multifocal progressive leukoencephalopathy
4) peripheral neuropathies.

In particular, with points 1, 2, 3 and 4 there is an associated constant diminution of the compounds essential for the metabolism of the myelinic structures (MTHF and SAMe) in the cephalorachidian fluid, with consequent perivenular and multifocal demyelination of the central nervous system.

On the basis of a series of already published data, there is no doubt of the therapeutic effectiveness of MTHF and FTHF and their pharmacologically acceptable salts in patients affected by specific genetic metabolic errors, such as deficiency of 5,10-tetrahydrofolate and dihydropterin reductase, which are associated with demyelination of the central nervous system and mental retardation (R. Surtees et al., The Lancet, vol. 335, March 1990).

The characteristics and advantages of the present invention will be more apparent from the summary description of a significant clinical trial selected from trials conducted using the compositions of the present invention.

EXPERIMENTAL PART

Figure 1:
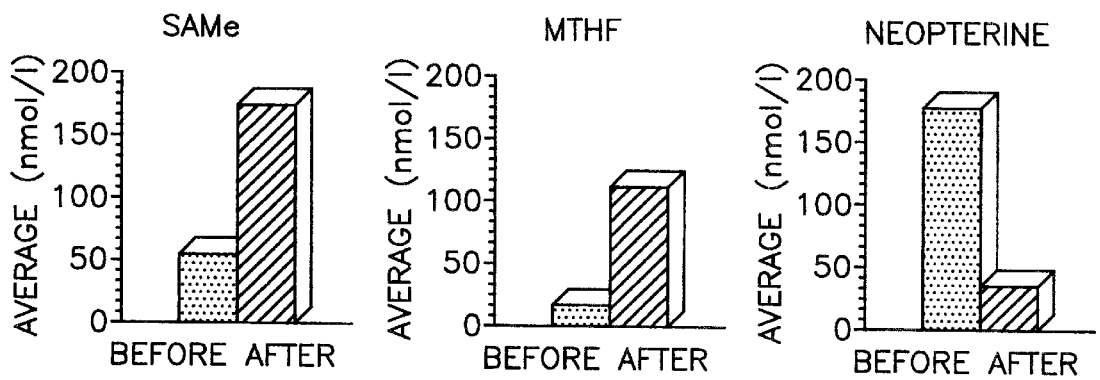
FIGS. 1 and 2 are graphical representations of levels of SAMe, MTHF and neopterine observed in cephalorachidian fluid samples taken during clinical trials before and after the treatments described in detail below.
Figure 1:
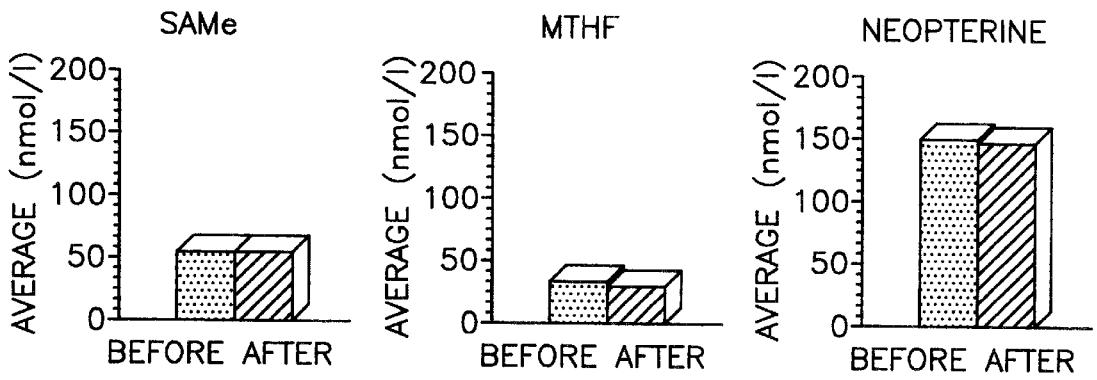

The purpose of the clinical trial reported below, using the double blind method with placebo controls, was to verify the therapeutic effects of administering MTHF and F7HF on clinical manifestations and on MTHF, SAMe and neopterin fluid concentration in AIDS sufferers with neurological complications.

20 hospitalized patients took part, these being of both sexes and aged between 24 and 41 years (average age 30.5) and for whom acquired immunodeficiency syndrome had been diagnosed in accordance with the definition of the Center for Disease Control, Atlanta, USA (Revision of the case definitions of acquired immunodeficiency syndrome for national reporting—United States Morbidity and Mortality Weekly Report 34:373–75, 1985). According to this definition, the patients pertained to Group IV, subgroup B (Table II). All patients had shown evident clinical signs and symptoms involving the central nervous system for at least one month.

The clinical and demographic characteristics of the 20 patients at the beginning of the study are shown in Table III.

No patient was under treatment with antiviral, antibiotic and/or sulphamide and immunomodulating drugs at the moment of commencement of the study.

At the commencement of the clinical trial the patients were subjected to lumbar puncture to exclude the existence of any infections of the central nervous system and/or to complete the diagnosis. On this same occasion the SAMe, MTHF and neopterin concentrations in the fluid were determined by high resolution liquid chromatography (HPLC). The values obtained were compared with those of a reference population of adult subjects subjected to lumbar puncture diagnosis for other neurological pathologies not related to alterations of the neopterin metabolism or of the transmethylation processes.

We examined the folate fluid concentration in the 20 HIV-positive patients and found that the levels of 5-MTHF and SAMe were low whereas the neopterin fluid levels were high in relation to the reference population (Table IV).

TABLE II

CLASSIFICATION SYSTEM FOR HIV INFECTION

| | |
|---|---|
| Group I | Acute infection |
| Group II | Asymptomatic infection |
| Group III | Persistent generalized lymphoadenopathy |
| Group IV | Other diseases |
| Subgroup A | Constitutional diseases |
| Subgroup B | Neurological diseases |
| Subgroup C | Secondary infective diseases |
| Category C-1 | Specific secondary infective diseases listed in the Center for Disease Control Surveillance Definition for AIDS |
| Category C-2 | Other specific secondary infective diseases |
| Subgroup D | Secondary tumours |
| Subgroup E | Other conditions |

TABLE III

DEMOGRAPHIC AND CLINICAL CHARACTERISTICS OF THE 20 PATIENTS AFFECTED BY AIDS (Group IV, Subgroup B) ON COMMENCING THE STUDY

| Patient | Age | Sex | CNS Symptoms | Treatment |
|---|---|---|---|---|
| 1 | 30 | M | Hyporeflexia Hypotonia, Babinski + | MTHF + SAMe |
| 2 | 24 | M | Spasticity | MTHF + SAMe |
| 3 | 41 | M | Initial dementia (ID) | Placebo |
| 4 | 29 | M | Hypotonia | Placebo |
| 5 | 32 | F | Hypotonia, DI, Hyporeflexia | MTHF + SAMe |
| 6 | 28 | M | Sensibility disturbance Babinski + | Placebo |
| 7 | 35 | F | Hypotonia, ID | Placebo |
| 8 | 31 | M | Spasticity, Babinski + Hyperreflexia | MTHF + SAMe |
| 9 | 25 | F | Hypotonia | SAMe |
| 10 | 28 | F | Babinski + | MTHF |
| 11 | 30 | M | Dementia | MTHF |
| 12 | 30 | M | Hyperreflexia | MTHF |
| 13 | 29 | M | Sensibility disturbance | SAMe |
| 14 | 32 | M | Hyperreflexia | SAMe |
| 15 | 36 | F | Babinski + | MTHF |
| 16 | 28 | M | Dementia | SAMe |
| 17 | 29 | M | Spasticity | FTHF |
| 18 | 34 | M | Dementia | FTHF |
| 19 | 24 | F | Hypotony | FTHF |
| 20 | 31 | M | Disturbed sensitivity | FTHF |

Group 1: patients 1, 2, 5, 8.
Group 2: patients 3, 4, 6, 7.
Group 3: patients 10, 11, 12, 15.
Group 4: patients 9, 13, 14, 16.
Group 5: patients 17, 18, 19, 20

TABLE IV

FLUID CONCENTRATIONS BEFORE COMMENCEMENT AND AT END OF STUDY

| Patient | SAMe (nmol/l) before/after | MTHF (nmol/l) before/after | Neopterins (nmol/1) before/after |
|---|---|---|---|
| 1 | 56/161* | 14/94* | 128/32* |
| 2 | 45/170* | 16/96* | 170/28* |
| 3 | 38/45° | 43/40° | 130/132° |
| 4 | 52/50° | 20/21° | 242/212° |
| 5 | 62/181* | 12/110* | 198/41* |
| 6 | 72/65° | 40/38° | 120/132° |
| 7 | 48/52° | 22/18° | 96/102° |
| 8 | 58/182* | 19/130* | 202/44* |
| 9 | 41/110$ | 15/18$ | 140/88$ |
| 10 | 36/125¢ | 18/76¢ | 210/97¢¢[24m |
| 11 | 35/96¢ | 24/69¢ | 131/53¢¢[24m |
| 12 | 31/89¢ | 36/112¢ | 220/62¢¢[24m |
| 13 | 50/162$ | 21/25$ | 172/64$ |
| 14 | 54/171$ | 41/44$ | 151/49$ |
| 15 | 48/91¢ | 33/89¢ | 159/57¢¢[24m |
| 16 | 29/115$ | 19/27$ | 184/51$ |
| 17 | 74/121L | 38/96L | 47/21L |
| 18 | 49/170L | 24/115L | 79/34L |
| 19 | 81/162L | 36/84L | 58/24L |
| 20 | 67/182L | 28/91L | 84/36L |

| | Reference population | | |
|---|---|---|---|
| Mean | 250 | 95 | 16 |
| Range | 172–450 | 20–211 | 3.2–47 |

\* = Group 1: patients 1, 2, 5, 8
° = Group 2: patients 3, 4, 6, 7
¢ = Group 3: patients 10, 11, 12, 15
$ = Group 4: patients 9, 13, 14, 16.
L = Group 5: patients 17, 18, 19 and 20

The patients were then randomly assigned to 5 groups for treatment lasting 4 weeks: Group 1 patients received SAMe 1,4-butane-disulphonate at a dose of 5–10 mg/kg/day i.v. plus MTHF at a dose of 0.5–1 mg/kg/day. Group 2 patients received indistinguishable placebo by the same administration method as SAMe and MTHF. Group 3 patients received MTHF, Group 4 patients received SAMe at the same doses as used for the treatment with these in association and Group 5 patients received FTHF.

Biochemical evaluation was done at the beginning and end of the study. After 4 weeks of treatment the folate and neopterin levels in the cephalorachidian fluid was measured (Table IV).

Figure 2:
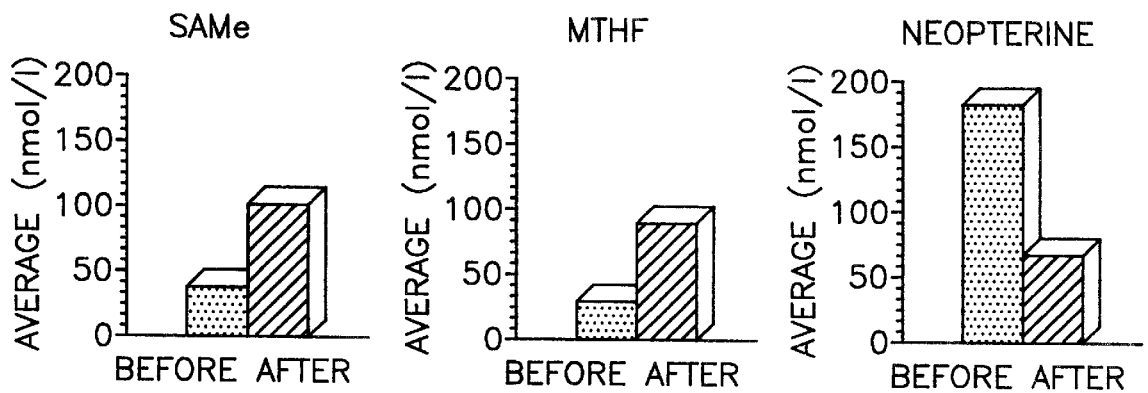
Figure 2:
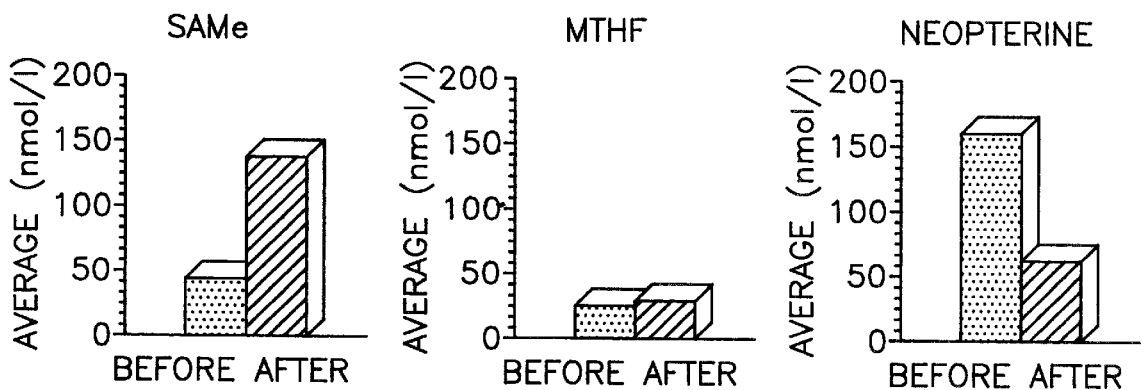

Statistical processing showed that the SAMe and MTHF values were significantly increased and neopterin values decreased in patients 1, 2, 5, 8, 10, 11, 12, 15, 17, 18, 19 and 20 (Groups 1, 3 and 5). Patients 9, 13, 14 and 16 (group 4) showed a significant increase in SAMe levels and a reduction in neopterin fluid levels but no significant increase in MTHF values with respect to the other groups. Patients 3, 4, 6 and 7 (Group 2) showed no significant variation in folate, SAMe or neopterin values in the cephalorachidian fluid with respect to the other groups (FIGS. 1, 2).

Certain scales suggested for investigating behaviour and mental functions were used for evaluating psychiatric symptoms. The evaluation of neurological symptoms was based on a clinical evaluation made at the commencement of treatment ($T_0$) and periodically each week ($T_1$, $T_2$, $T_3$ and $T_4$).

Specifically, the following scales were used:
1) Wechsler Adult intelligence Scale (WAIS)
2) Digit Span (Wechsler Adult intelligence Scale Manual, Psychological Corporation, New York 1955), which consists of a forward and backward repetition of numerical sequences of increasing length read by the examiner to the patient.

The following were also evaluated as specific neurological disturbance parameters:

a) babinski reflex
b) superficial and "profundus" sensitivity disturbances.

These tests were conducted before the commencement of treatment ($T_0$) and at the end of treatment ($T_4$).

The psychometric tests showed a general diminution of intellectual, mnemonic and verbal capacity, with serious short-term memory compromise in the 20 patients before the study.

The W.A.I.S. mean value for the 20 patients under examination was:
verbal: 84
performance: 89
total: 85.

Within the first week of treatment the patients of Groups 1, 3, 4 and 5 showed a marked elevation in mood and an improvement in mnemonic and attentive capacity. Within two weeks of treatment the neurological examination showed an improvement in pyramidal weakness and a diminution in pathological reflexes. At time $T_4$ the mean W.A.I.S. values for Groups 1, 3, 4 and 5 were:
verbal: 104 (+20)
performance: 98 (+9)
total: 102 (+18).

In contrast, group 2 (placebo) showed no significant improvement in W.A.I.S. values, the mean of these being as follows:
verbal: 83
performance: 88
total: 84.

Likewise no significant modifications in neurological symptomatology were recorded for this group (Table V).

TABLE V

NEUROLOGICAL SIGNS AT TIME $T_4$

| Patient | Babinski* | Sensitivity° | Dementia* |
|---|---|---|---|
| 1 | – | no | – |
| 2 | – | no | – |
| 3 | + | yes | + |
| 4 | + | yes | + |
| 5 | – | no | – |
| 6 | ± | yes | + |
| 7 | + | yes | + |
| 8 | – | no | – |
| 9 | – | no | – |
| 10 | – | no | – |
| 11 | – | no | ± |
| 12 | – | no | – |
| 13 | – | no | – |
| 14 | – | no | – |
| 15 | – | no | – |
| 16 | – | no | – |
| 17 | – | no | – |
| 18 | – | no | ± |
| 19 | – | no | – |
| 20 | – | no | – |

Legend:
*(+) present (–) absent
°disturbances of superficial and profundus sensitivity

TABLE VI

OVERALL JUDGEMENT ON EFFECTIVENESS OF TREATMENTS

| | Worsened | Unchanged | Improved | Much improved |
|---|---|---|---|---|
| TIME 1 WEEK ($T_1$) | | | | |
| MTHF + SAMe | — | 2 | 2 | — |
| SAMe | — | 2 | 2 | — |
| MTHF | — | 2 | 2 | — |
| Placebo | — | 3 | 1 | — |
| FTHF | — | 3 | 1 | — |
| TIME 2 WEEKS ($T_2$) | | | | |
| MTHF + SAMe | — | 1 | 3 | — |
| SAMe | — | 1 | 3 | — |
| MTHF | — | 1 | 3 | — |
| Placebo | 1 | 3 | — | — |
| FTHF | — | 1 | 3 | — |
| TIME 4 WEEKS ($T_4$) | | | | |
| MTHF + SAMe | — | — | 3 | 1 |
| SAMe | — | 1 | 3 | — |
| MTHF | — | — | 3 | 1 |
| Placebo | 1 | 3 | — | — |
| FTHF | — | 1 | 3 | — |

Results

The psychometric tests, including the W.A.I.S., showed statistically significant improvements in groups 1, 3, 4 and 5 by the effect of the treatment with MTHF, FTHF and SAMe in association or in individual administration according to the present invention. In particular, at times $T_3$ and $T_4$ the W.A.I.S. test, the forward Digit Span test and the backward digit Span test showed a statistically significant difference.

In contrast, the group of patients treated with placebo (Group 2) showed no modification of any kind. Tolerance during treatment was good for nearly all patients except for one subject of Group 1 (patient 2) who complained of slight nausea during the initial days of treatment. This condition was resolved spontaneously and disappeared later, even though administration of the medicament continued.

Table VI shows the overall judgement on the effectiveness of the treatment at times $T_1$, $T_2$ and $T_4$ as expressed by the medical practitioner who effected the therapy. In formulating this judgement the medical practitioner also took account of indications by the patients' relatives and by the paramedical personnel. The number of positive responses to treatment with MTHF and SAMe either in association or in monotherapy was found to be already statistically significant at $T_2$ and increased further at $T_4$ (68% of positive responses to the treatment).

The pharmaceutical compositions of the present invention containing the three products as active principles, alone or in admixture also with pharmaceutically acceptable, solid or liquid excipients and auxiliary agents are suitable for use in injectable or oral form.

As the combination of the three active principles in single formulation is generally not sufficiently stable with time, it is advisable to prepare the combination extemporaneously at the moment of use from pharmaceutical formulations of the individual active principles.

The three separate active principles can also be administered to the patient, either simultaneously or a short time apart. The pharmaceutical compositions according to the present invention can be in the form of a lyophilized vial coupled with the appropriate solvent, lyophilized bottles also coupled with the appropriate solvent, injectable solutions, tablets, pills, capsules, delayed release capsules, delayed release tablets, gastroresistant tablets, sachets, extemporaneous syrups, delayed release syrups and other forms normally used in the pharmaceutical field, with a total active principle contents of between 20 and 2000 mg.

As non-limiting illustration of the invention the following examples are given of pharmaceutical compositions of the individual active principles SAMe, 5-MTHF and 5-FTHF which can be mixed together at the moment of administration to form the association of the active principles according to the present invention.

Pharmaceutical Compositions Containing a Single Active Principle

EXAMPLE 1

Injectable preparations containing 200 mg of SAMe as active principle.

| A) A bottle contains: | | |
|---|---|---|
| SAMe disulphate-p-toluenesulphonate | | *384 mg |
| *equivalent to 200 mg SAMe ion | | |
| Mannitol | | 240 mg |
| A solvent vial contains: | | |
| L-lysine | | 300 mg |
| Sodium hydroxide | | 9 mg |
| $H_2O$ for injectables | to make up to | 5 ml |
| B) A bottle contains: | | |
| SAMe 1,4-butanedisulphonate | | *394 mg |
| *equivalent to 200 mg SAMe ion | | |
| A vial contains: | | |
| L-lysine | | 160 mg |
| Sodium hydroxide | | 4.5 mg |
| $H_2O$ for injectables | to make up to | 2.5 ml |
| C) A bottle contains: | | |
| SAMe 2,5-sulphate | | *333 mg |
| *equivalent to 200 mg ion | | |
| A solvent vial contains: | | |
| L-lysine | | 320 mg |
| Sodium hydroxide | | 2 mg |
| $H_2O$ for injectables | to make up to | 5 ml |

EXAMPLE 2

Injectable preparations containing 400 mg of SAMe as active principle.

| A) A bottle contains: | | |
|---|---|---|
| SAMe disulphate-p-toluenesulphonate | | *768 mg |
| *equivalent to 400 mg ion | | |
| A solvent vial contains: | | |
| L-lysine | | 600 mg |
| Sodium hydroxide | | 18 mg |
| $H_2O$ for injectables | to make up to | 10 ml |
| B) A bottle contains: | | |
| SAMe 1,4-butanedisulphonate | | *788 mg |
| *equivalent to 400 mg ion | | |
| A vial contains: | | |
| L-lysine | | 305 mg |
| Sodium hydroxide | | 2.1 mg |
| $H_2O$ for injectables | to make up to | 5 ml |
| C) A bottle contains: | | |
| SAMe 2,5-sulphate | | *640 mg |
| *equivalent to 400 mg ion | | |
| A solvent vial contains: | | |
| L-lysine | | 640 mg |
| Sodium hydroxide | | 4 mg |
| $H_2O$ for injectables | to make up to | 5 ml |

EXAMPLE 3

Injectable preparations containing 50 mg of 5-methyl-tetrahydrofolic acid as active principle.

| A) A bottle contains: | | |
|---|---|---|
| (±)L-5-methyl-5,6,7,8-tetrahydrofolic acid (MTHF) | | |
| calcium salt | | *55 mg |
| *equivalent to 50 mg acid | | |
| Glutathione | | 10 mg |
| Citric acid | | 30 mg |
| Mannitol | | 170 mg |
| Methyl-p-hydroxybenzoate | | 1 mg |
| Sodium hydroxide | | 17.7 mg |
| A solvent vial contains: | | |
| $H_2O$ for injectables | to make up to | 3.3 ml |
| B) a phial contains: | | |
| (−)-L-5-methyl-5,6,7,8-tetrahydrofolic acid | | |
| calcium salt | | 55 mg* |
| *equal to 50 mg acid | | |
| Glutathione | | 10 mg |
| Citric acid | | 30 mg |
| Mannitol | | 170 mg |
| Methyl-p-hydroxybenzoate | | 1 mg |
| Sodium hydroxide | | 17.7 mg |
| A solvent vial contains: | | |
| $H_2O$ for injection q.s. to | | 3.3 ml |

EXAMPLE 4

Injectable compositions containing 50 mg (±)-L-5-formyl-5,6,7,8-tetrahydrofolic acid (or folinic acid) as an active principle.

| A) A phial contains: | |
|---|---|
| Calcium folinate | 55 mg |
| *equal to 50 mg folinic acid | |
| Glutathione | 10 mg |
| Citric acid | 30 mg |
| Mannitol | 170 mg |
| Methyl-p-hydroxybenzoate | 1 mg |
| Sodium hydroxide | 17.7 mg |
| A solvent vial contains: | |
| $H_2O$ for injection q.s. to | 3.3 ml |

EXAMPLE 5

Injectable compositions containing 50 mg (−)-L-5-formyl-5,6,7,8-tetrahydrofolic acid as an active principle.

| A) A phial contains: | |
|---|---|
| Calcium folinate | 55 mg |
| *equal to 50 mg acid | |
| Glutathione | 10 mg |
| Citric acid | 30 mg |
| Mannitol | 170 mg |
| Methyl-p-hydroxybenzoate | 1 mg |
| Sodium hydroxide | 17.7 mg |
| A solvent vial contains: | |
| H₂O for injection q.s. to | 3.3 ml |
| Oral preparations | |

EXAMPLE 6

Oral preparations containing 200 mg of SAMe as active principle.

| A) CORE: | |
|---|---|
| SAMe disulphate-p-toluenesulphonate | *384 mg |
| *equivalent to 200 mg SAMe ion | |
| Mannitol | 130 mg |
| Levilite | 10 mg |
| Sodium bicarbonate | 10 mg |
| Mg stearate | 7 mg |
| COATING: | |
| Polyvinylpyrrolidone | 4 mg |
| Diethylphthalate | 2 mg |
| FILM: | |
| Cellulose acetophthalate | 12.76 mg |
| Diethylphthalate | 4.09 mg |
| Silicone HK 15A | 1.15 mg |
| B) CORE: | |
| SAMe 1,4-butanedisulphonate | *394 mg |
| *equivalent to 200 mg ion | |
| Microcrystalline cellulose (AVICEL PH 102) | 98 mg |
| Silica (AEROSIL 200) | 1 mg |
| Mg stearate | 7 mg |
| FILM: | |
| Cellulose acetophthalate | 12.76 mg |
| Diethylphthalate | 4 mg |
| Silicone HK 15A | 1.15 mg |

EXAMPLE 7

Oral preparations containing 400 mg of SAMe as active principle.

| A) CORE: | |
|---|---|
| SAMe 2,5-sulphate | *688 mg |
| *equivalent to 400 mg ion | |
| Silica (AEROSIL 200) | 3 mg |
| Microcrystalline cellulose (AVICEL PH 102) | 215 mg |
| Mg stearate | 14 mg |
| FILM: | |
| Cellulose acetophthalate | 25.52 mg |
| Diethylphthalate | 8.18 mg |
| Silicone HK 15A | 2.30 mg |

EXAMPLE 8

Oral preparations containing 50 mg of 5-methyl-tetrahydrofolic acid as active principle.

| A) CORE: | |
|---|---|
| (±)-L-5 methyl-5,6,7,8-tetrahydrofolic acid | |
| calcium salt | *55 mg |
| *equivalent to 50 mg acid | |
| Microcrystalline cellulose (AVICEL PH 102) | 80 mg |
| Spray-dryed lactose | 56 mg |
| Mg stearate | 2 mg |
| FILM: | |
| Cellulose acetophthalate | 8.5 mg |
| Silicone HK 15A | 0.75 mg |

EXAMPLE 9

Oral preparation containing 50 mg of (±)-L-5-formyl-5,6,7,8-tetrahydrofolic acid.

| A) CORE: | |
|---|---|
| Calcium folinate | *55 mg |
| *equivalent to 50 mg acid | |
| Microcrystalline cellulose (AVICEL PH 102) | 80 mg |
| Spray-dryed lactose | 51 mg |
| Mg stearate | 2 mg |
| FILM: | |
| Cellulose acetophthalate | 8.5 mg |
| Diethylphthalate | 2.75 mg |
| Silicone HK 15A | 0.75 mg |

EXAMPLE 10

Oral preparation cotnaining 50 mg methyltetrahydrofolic acid as an active principle:

| A) NUCLEUS | |
|---|---|
| (−)-L-5-methyl-5,6,7,8-tetrahydrofolic acid | |
| calcium salt | 55 mg* |
| *equal to 50 mg acid | |
| Microcrystalline cellulose (AVICEL PH 102) | 80 mg |
| Spray dried lactose | 56 mg |
| Mg stearate | 2 mg |
| FILMING | |
| Cellulose acetophthalate | 8.5 mg |
| Silicone HK 15A | 0.75 mg |

EXAMPLE 11

Oral preparation containing 50 mg (−)-L-5-formyl-5,6,7,8-tetrahydrofolic acid as an active principle.

| A) NUCLEUS | |
|---|---|
| Calcium folinate | 55 mg* |
| *equal to 50 mg acid | |
| Microcrystalline cellulose (AVICEL PH 102) | 80 mg |
| Spray dried lactose | 51 mg |
| Mg stearate | 2 mg |

-continued

FILMING

| | |
|---|---|
| Celluloseacetophthalate | 8.5 mg |
| Diethylphthalate | 2.75 mg |
| Silicone HK 15A | 0.75 mg |

What is claimed is:

1. A therapeutic method for treating neurological affections selected from the group consisting of subacute encephalitis associated with dementia and vacuolar myelopathies comprising administering to a patient in need thereof a therapeutically effective amount of at least one member selected from the group consisting of S-adenosyl-methionine salt, 5-methyltetrahydrofolic acid and 5-formyltetrahydrofolic acid.

2. A therapeutic method according to claim 1, wherein the S-adenosyl-methionine salt is administered at the same time or at close intervals with 5-methyltetrahydrofolic acid or with 5-formyltetrahydrofolic acid.

3. A therapeutic method according to claim 2, wherein the S-adenosyl-methionine is administered at doses of between 100 and 2,000 mg/day.

4. A therapeutic method according to claim 2, wherein the 5-methyltetrahydrofolic acid or the 5-formyltetrahydrofolic acid is administered at doses ranging between 20 and 200 mg/day.

5. A therapeutic method according to claim 3, wherein the 5-methyltetrahydrofolic acid or the 5-formyltetrahydrofolic acid is administered at doses ranging between 20 and 200 mg/day.

6. A therapeutic method according to claim 1, wherein the S-adenosyl-methionine (SAMe) salt is administered at the same time or at close intervals with 5-methyltetrahydrofolic acid (MTHF) or with 5-formyltetrahydrofolic acid (FTHF) and at a weight ratio of SAMe to MTHF or FTHF ranging from 10:1 to 4:1, respectively.

7. A therapeutic method according to claim 6 wherein said weight ratio is 8:1.

8. A therapeutic method according to claim 1 wherein the S-adenosylmethionine is administered at doses ranging from 100 and 2000 mg/day.

9. A therapeutic method according to claim 8 wherein the S-adenosylmethionine is administered at the dose of 400 mg/day.

10. A therapeutic method according to claim 1 wherein 5-methyltetrahydrofolic or 5-formyltetrahydrofolic acid is administered at doses ranging from 20 and 200 mg/day.

11. A therapeutic method according to claim 10 wherein 5-methyltetrahydrofolic or 5-formyltetrahydrofolic acid is administered at the dose of 50 mg/day.

* * * * *